(12) United States Patent
Buelna et al.

(10) Patent No.: US 6,620,177 B2
(45) Date of Patent: Sep. 16, 2003

(54) ANASTOMOSIS OCCLUSION DEVICE

(75) Inventors: Terrence Buelna, San Francisco, CA (US); Adam Gold, Sunnyvale, CA (US); Thomas J. Fogarty, Portola Valley, CA (US); Thomas Howell, Palo Alto, CA (US); Russell J. Anderson, Union City, CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 0 days.

(21) Appl. No.: 09/887,477

(22) Filed: Jun. 22, 2001

(65) Prior Publication Data

US 2002/0116017 A1 Aug. 22, 2002

Related U.S. Application Data

(60) Provisional application No. 60/282,545, filed on Apr. 9, 2001, and provisional application No. 60/270,946, filed on Feb. 21, 2001.

(30) Foreign Application Priority Data

Feb. 15, 2001 (TW) .................................... 90202276 U

(51) Int. Cl.[7] .............................................. A61B 17/08
(52) U.S. Cl. .................. 606/153; 606/194; 606/213
(58) Field of Search .............................. 606/153, 157, 606/158, 191, 198, 200, 213, 215–217, 194; 604/174; 128/898

(56) References Cited

U.S. PATENT DOCUMENTS

| | | |
|---|---|---|
| 1,501,428 A | 7/1924 | Wisoff |
| 4,559,944 A | 12/1985 | Jaeger |
| 4,817,287 A | 4/1989 | Arnold et al. |
| 5,122,122 A * | 6/1992 | Allgood ...................... 604/174 |
| 5,330,497 A | 7/1994 | Freitas et al. |
| 5,447,515 A | 9/1995 | Robicsek |
| 5,501,692 A | 3/1996 | Riza |
| 5,599,329 A | 2/1997 | Gabbay |
| 5,613,976 A | 3/1997 | Agee et al. |
| 5,676,670 A | 10/1997 | Kim |
| 5,697,937 A | 12/1997 | Toma |
| 5,797,934 A | 8/1998 | Rygaard |
| 5,913,870 A | 6/1999 | DeFonzo et al. |
| 5,921,996 A | 7/1999 | Sherman |
| 5,944,730 A | 8/1999 | Nobles et al. |
| 5,954,735 A | 9/1999 | Rygaard |
| 5,957,363 A | 9/1999 | Heck |
| 6,015,416 A | 1/2000 | Stefanchik et al. |
| 6,017,352 A | 1/2000 | Nash et al. |
| 6,030,406 A | 2/2000 | Davis et al. |
| 6,042,563 A | 3/2000 | Morejohn et al. |
| 6,132,440 A | 10/2000 | Hathaway et al. |
| 6,135,981 A | 10/2000 | Dyke |
| 6,143,015 A | 11/2000 | Nobles |
| 6,149,583 A | 11/2000 | Vierra et al. |
| 6,171,319 B1 | 1/2001 | Nobles et al. |
| 6,183,486 B1 | 2/2001 | Snow et al. |
| 6,187,019 B1 | 2/2001 | Stefanchik et al. |
| 6,203,559 B1 | 3/2001 | Davis et al. |
| 6,210,365 B1 | 4/2001 | Afzal |

FOREIGN PATENT DOCUMENTS

| | | |
|---|---|---|
| EP | 0 894 475 A1 | 2/1999 |
| WO | WO 99/08603 | 7/1998 |

* cited by examiner

*Primary Examiner*—Julia W. Woo
(74) *Attorney, Agent, or Firm*—Morrison & Foerster LLP

(57) ABSTRACT

An anastomosis occlusion device having a low-profile shaft assembly configured for insertion into the lumen of a vessel. The device includes an expandable region at the shaft assembly distal end with a sealing membrane that spans the expandable region, and a corresponding clamping member moveable toward the expandable region. Once inserted into the vessel lumen the expandable region is deployed from a first low-profile position into a second expanded position, and positioned at the target site of the anastomosis. Movement of the distal end of the clamping member, which remains located outside the vessel, against the expanded region creates a seal at the target site.

30 Claims, 11 Drawing Sheets

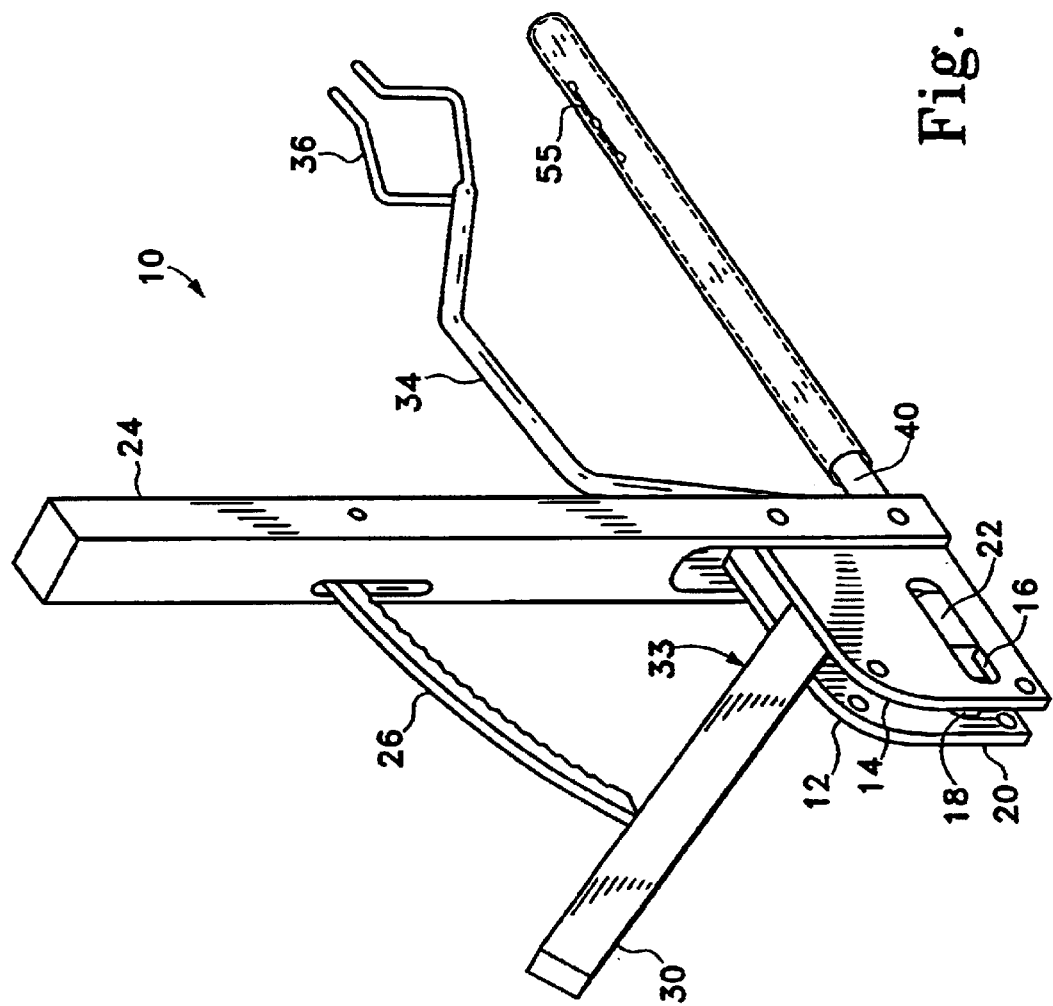

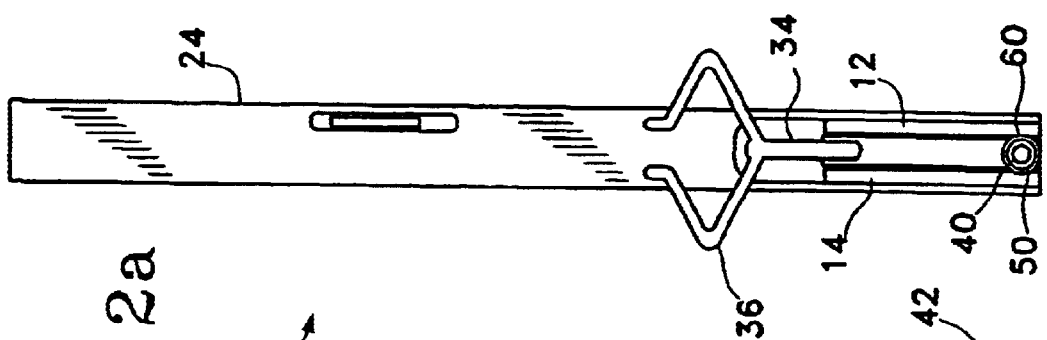
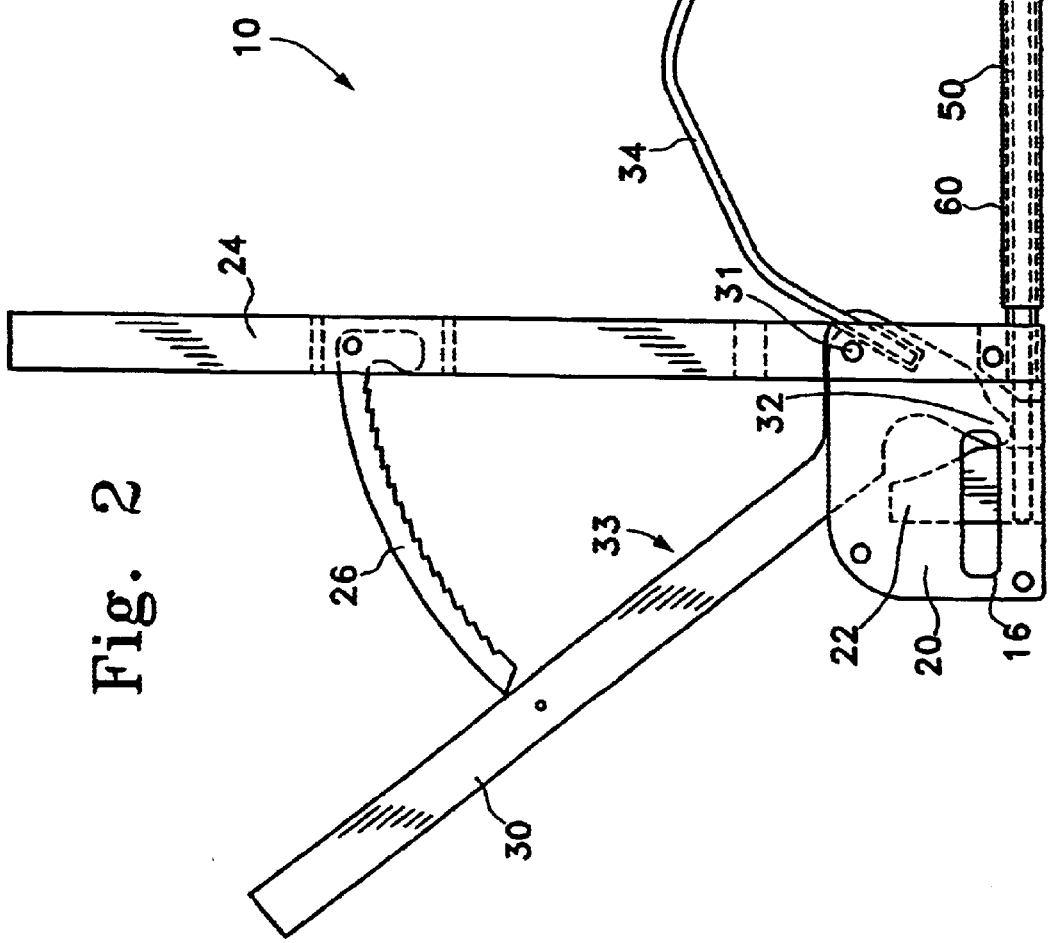

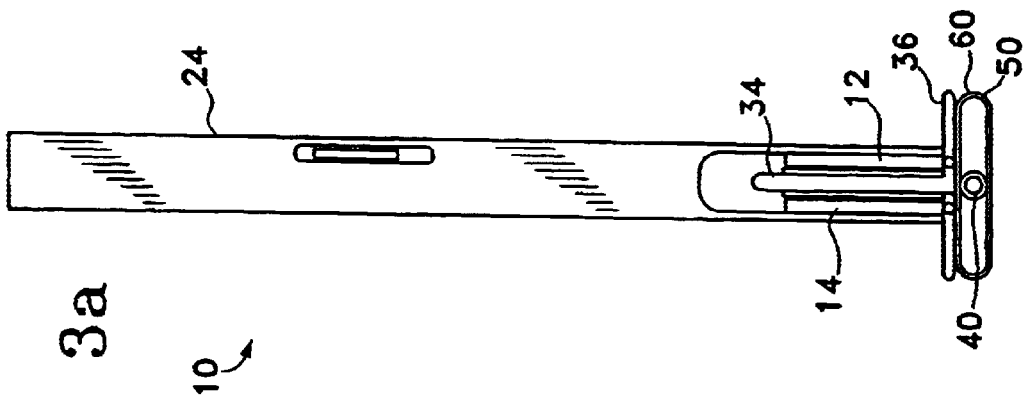
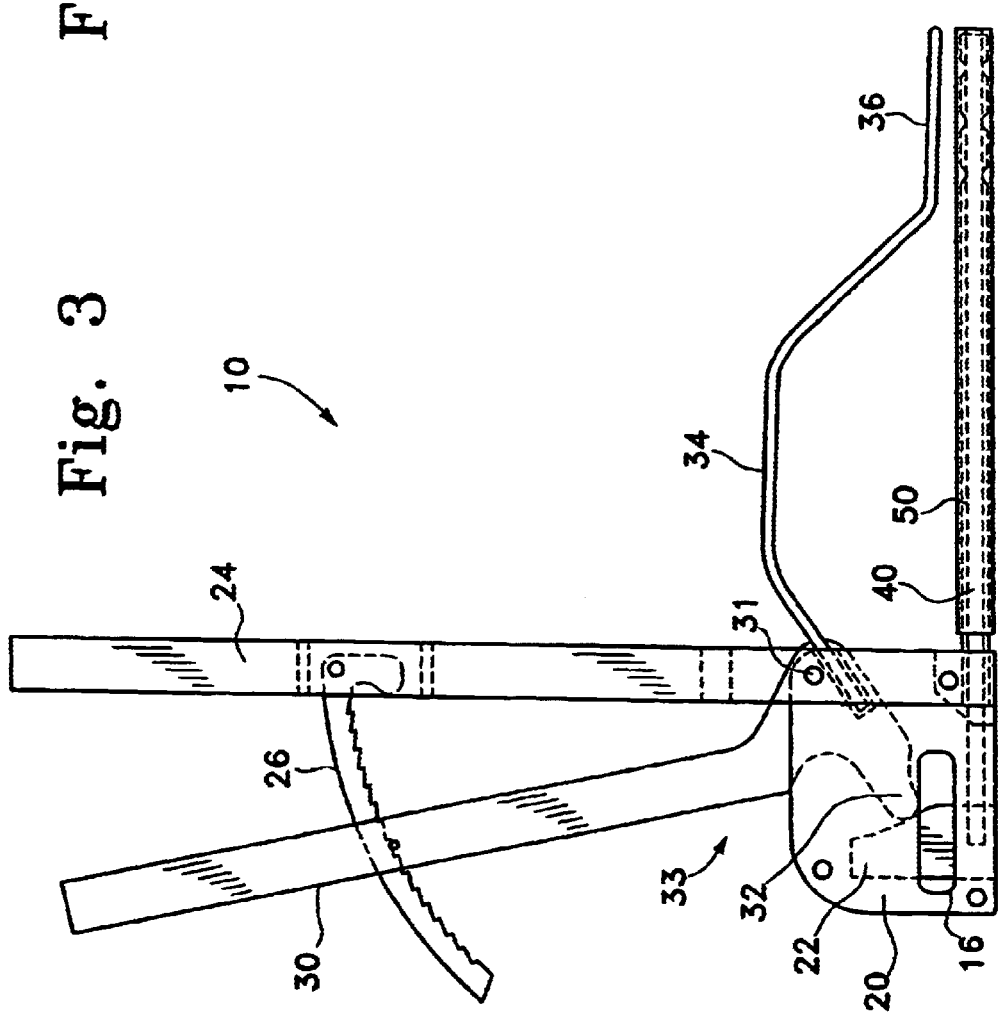

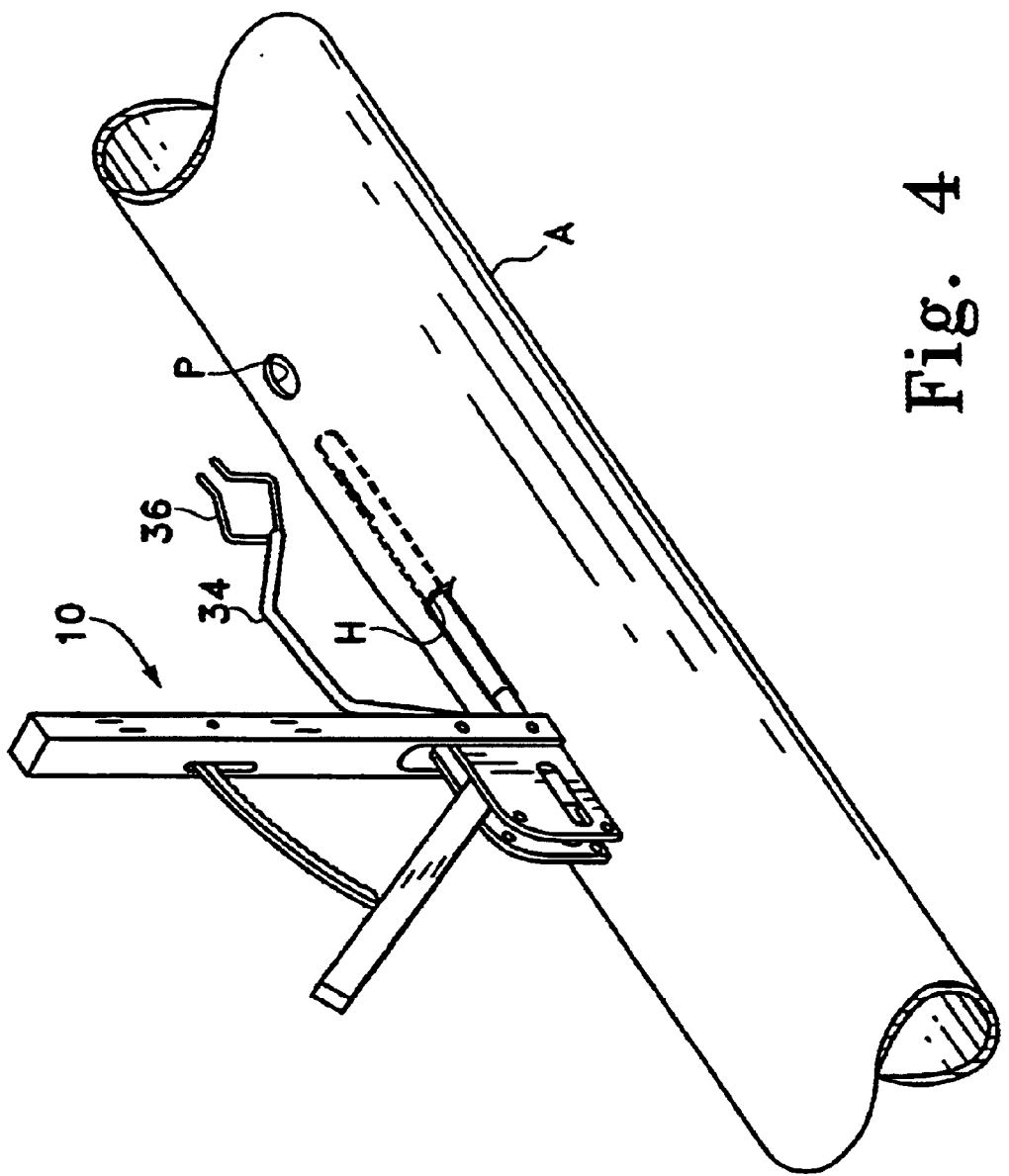

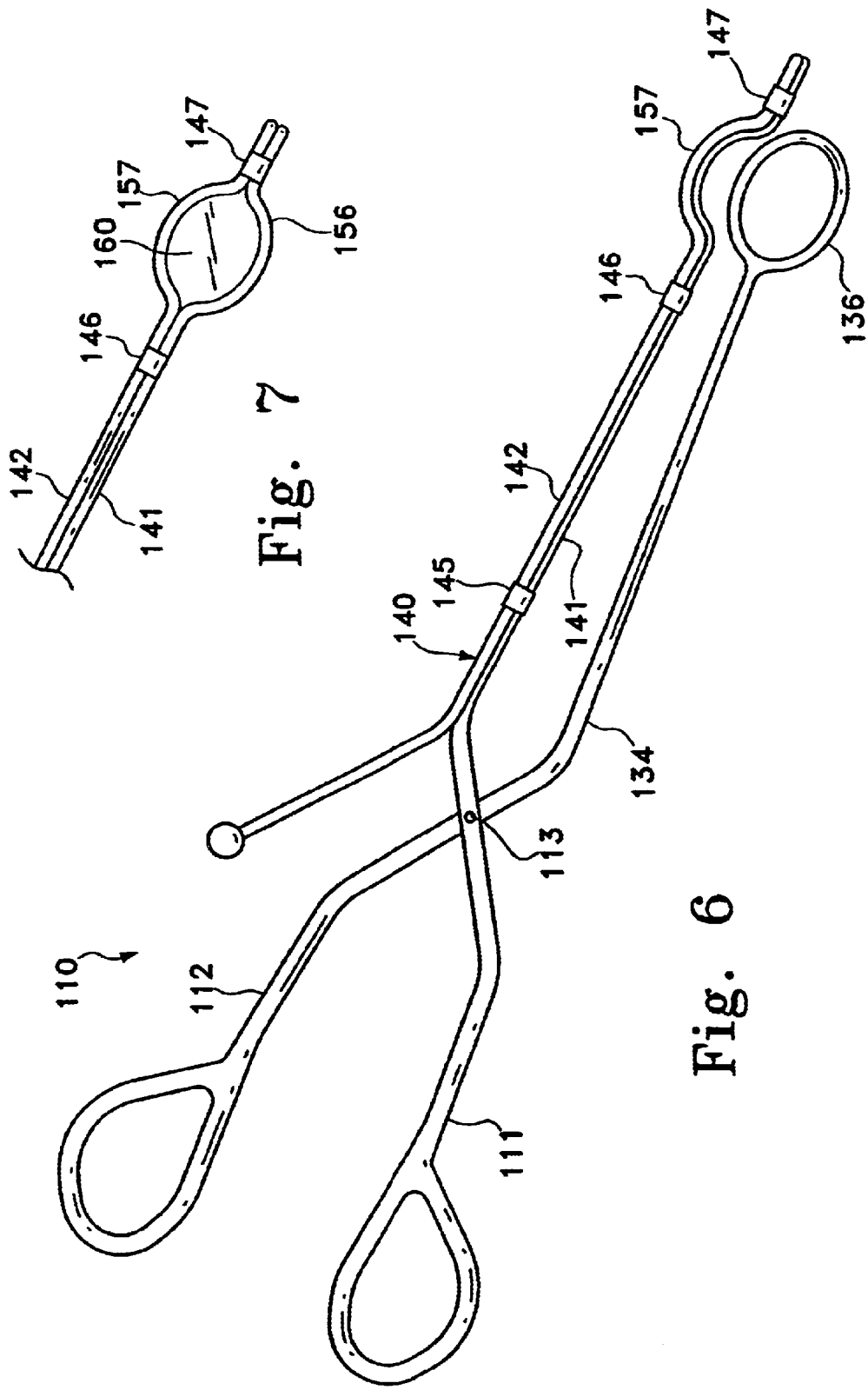

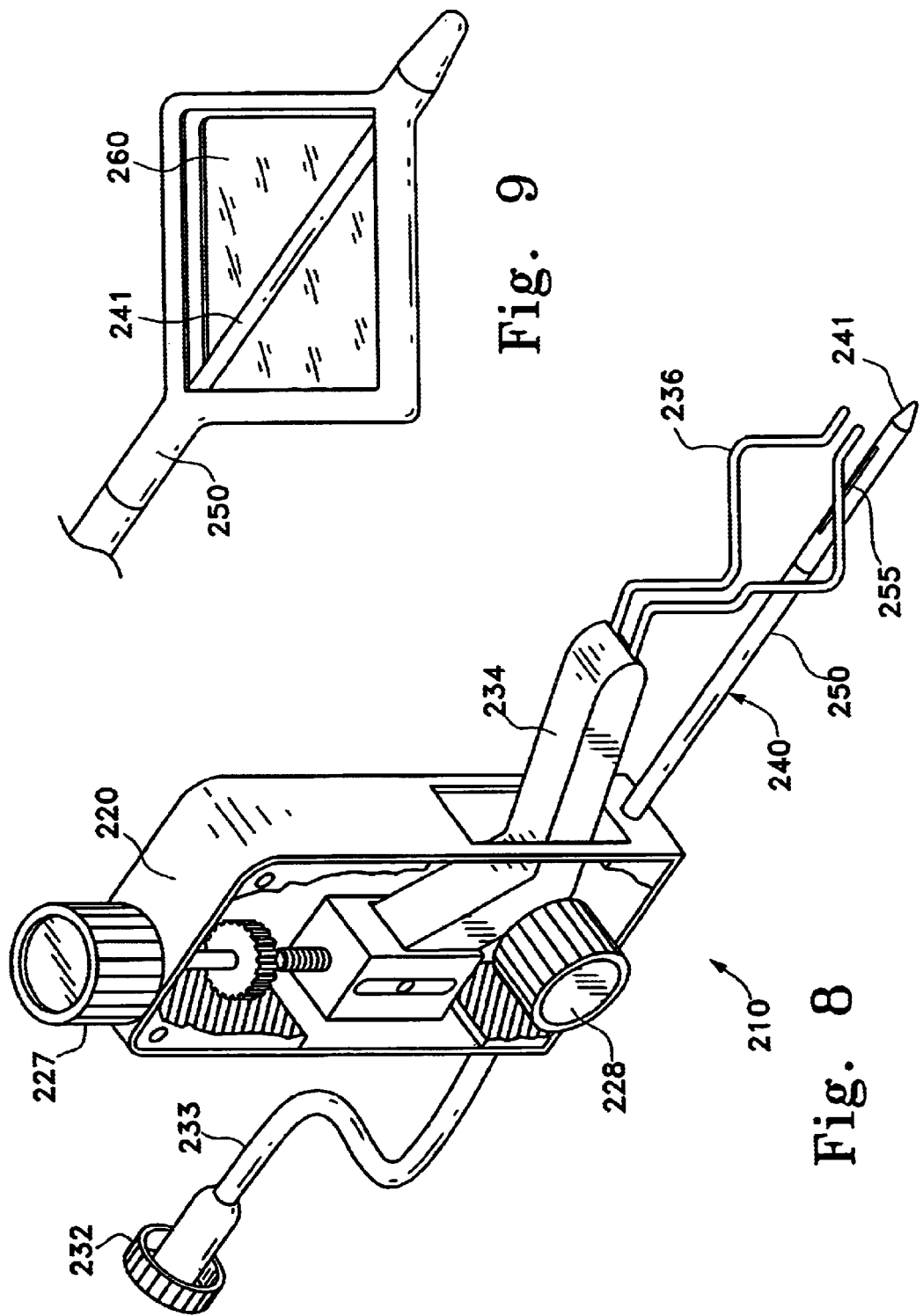

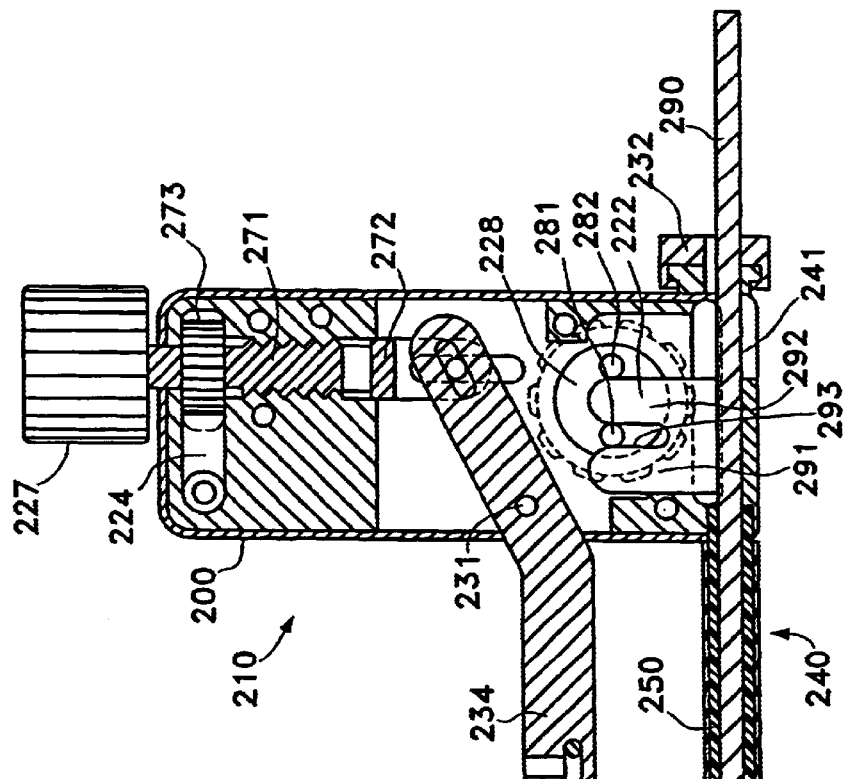
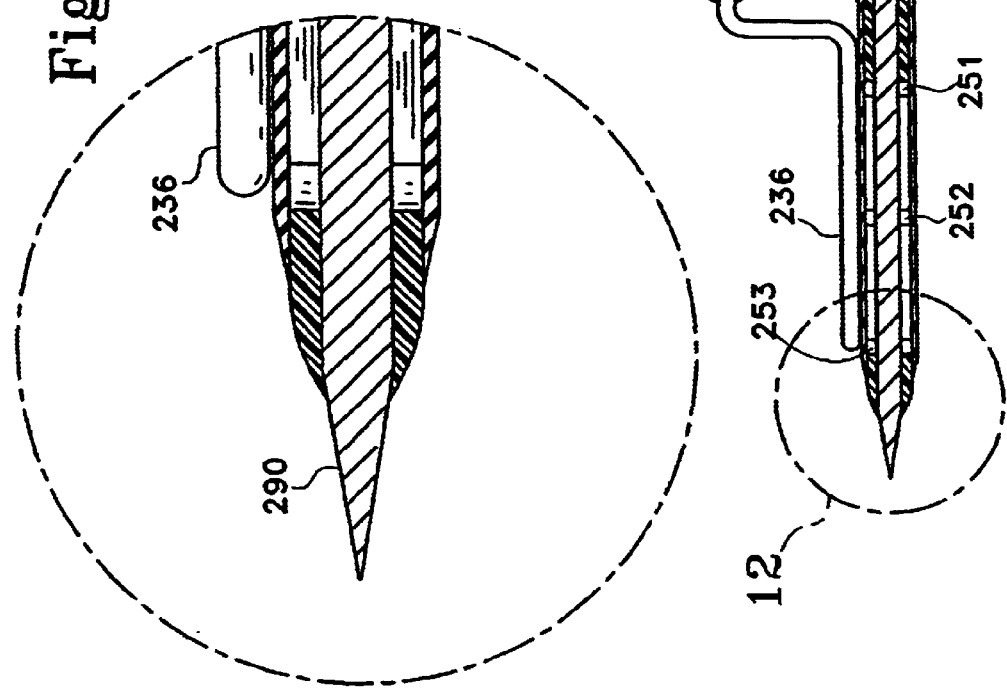

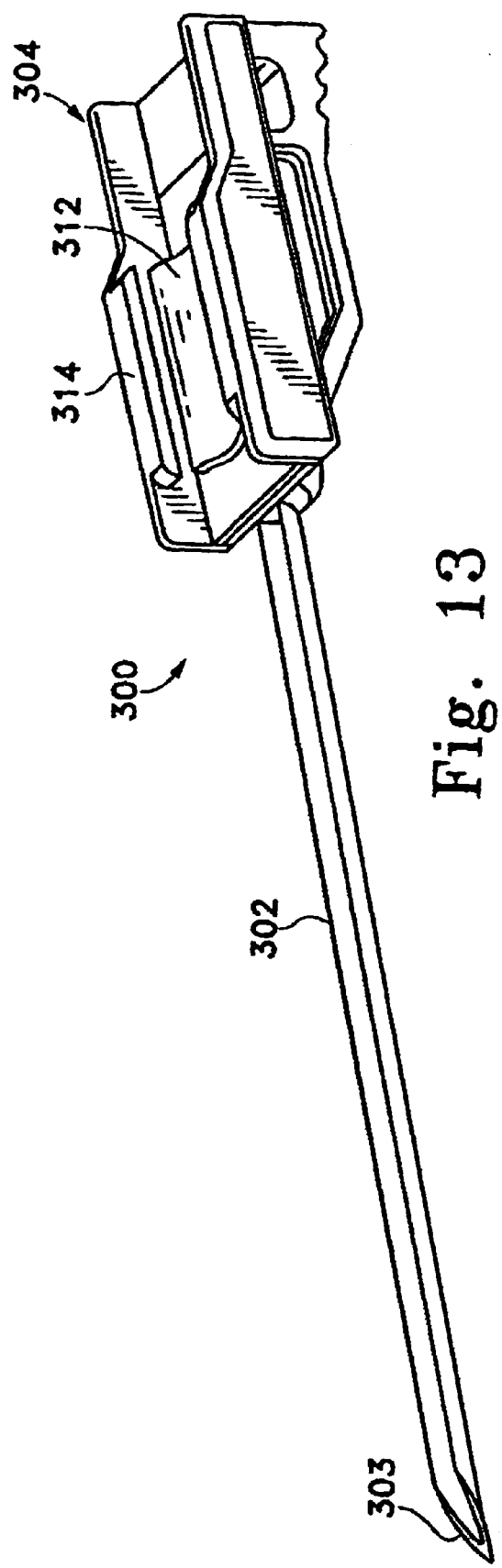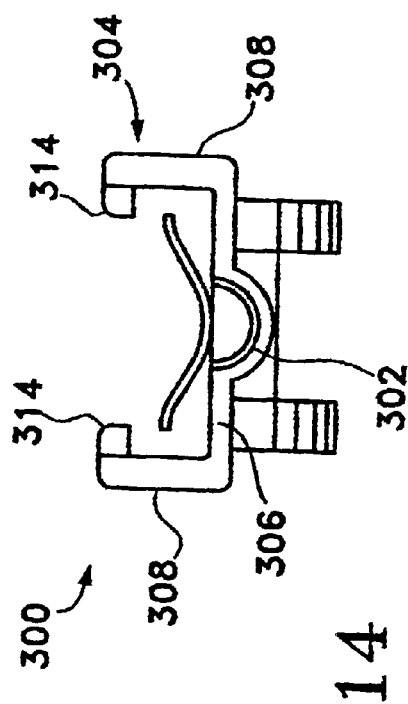
Fig. 13
Fig. 14

ANASTOMOSIS OCCLUSION DEVICE

This application claims benefit of priority under 35 U.S.C. §119(e) of U.S. Provisional Application No. 60/282,545, filed Apr. 9, 2001, and U.S. Provisional Application No. 60/270,946, filed Feb. 21, 2001, each of which is incorporated herein in its entirety.

BACKGROUND OF THE INVENTION

The present invention relates to the fields of vascular and cardiovascular surgery, and more particularly to methods and devices for obtaining arterial or vascular occlusion when performing graft procedures.

Vascular and cardiovascular grafting procedures typically require the complete, or at least partial, occlusion of a selected vessel. For example, in the field of cardiovascular surgery, coronary artery bypass graft (CABG) procedures involving proximal anastomosis require the full, or at least partial, occlusion of the aorta. During proximal anastomosis, a vein or arterial graft is sewn to the aorta for revascularization of diseased or otherwise compromised coronary arteries. The internal mammary artery and radial artery of the arm are also used as bypass vessels. Occlusion of the aorta is typically accomplished by clamping. A variety of clamp configurations are in common use, including cross-clamps for partial occlusion procedures. For procedures involving cardiopulmonary bypass, full aortic occlusion is required. Partial occlusion is used in either on or off-pump coronary artery bypass graft procedures for proximal anastomosis. Occlusion of the aorta prevents blood flow from entering the graft target site, creating a bloodless field for the surgeon to then sew the graft to the aorta. Once the graft is sewn to the aorta, the surgeon removes the clamp, once again allowing blood flow to the anastomotic region.

Unfortunately, injury resulting from such clamping can be significant. Such injuries include, but are not limited to, intimal hyperplasia, thrombosis (which may progress to total occlusion), embolism, intimal tears and flaps, mural dissections, aneurysms, arterial rupture, through-and through injury, and arterio-venous fistulae. As just one example, neurologic morbidity after cardiac surgery has been associated with particulate embolization. Crossclamp manipulation has been identified as the single most significant cause of particulate emboli release during cardiac surgery. Therefore, surgeons would prefer to eliminate the use of clamps during coronary artery bypass graft procedures in order to minimize adverse events and improve outcomes.

Efforts have been made to devise alternative devices and methods for performing bypass graft procedures that avoid complete clamping or crossclamping of the aorta. For example, U.S. Pat. No. 5,477,515 describes a bypass clamp with a spoon-shaped blade insertable through an incision in the aorta. Patches of saphaneous vein or other substitute are sutured on either side of the incision to reinforce the aorta and prevent tearing or abrasion by the clamp. U.S. Pat. No. 5,944,730 describes a device for creating a seal at an incision that includes a tube with a translatable shaft connected to a flexible inverting member. The inverting member is inserted into the incision and proximal force applied to the device creates a seal. Other methods have relied upon inflatable devices for partially occluding a vessel without interrupting blood flow. U.S. Pat. No. 6,143,015 describes such a device which includes first and second inflatable spaced apart members interconnected by a tubular connector that allows for blood flow.

Despite these efforts, there remains a need to provide for an anastomosis occlusion device that minimizes the adverse events associated with conventional clamping and cross-clamping techniques, avoids trauma to the vessel and graft site, and that is versatile, and easy-to-use.

SUMMARY OF THE INVENTION

The present invention meets the above needs and achieves further advantages by providing for an anastomosis occlusion device and methods for use in grafting procedures that minimize trauma and adverse events associated with grafting procedures, including trauma and adverse events currently associated with coronary artery bypass graft procedures.

In particular, the invention provides for a low-profile shaft assembly that is configured for insertion into the lumen of the aorta (or other selected vessel) and that includes an expandable region at the distal end of the shaft assembly. The expandable region includes a sealing membrane that spans across the expandable region. Once inserted into the lumen of the aorta (or other selected vessel) this expandable region can be deployed from a first low-profile position into a second expanded position, and positioned at the target site of the anastomosis. A clamping member, located outside the vessel, is also provided having a distal end that is shaped to correspond to the expandable region of the shaft assembly in its second expanded position. Movement of the distal end of the clamping member against the expanded region creates a seal at the target site, defined by the border of the expanded region of the shaft assembly and the sealing membrane. This sealed-off area is thus temporarily segregated from bloodflow at the target site to facilitate performing a grafting procedure without undue blood pressure or leakage interfering with the procedure.

One of the many advantages of the invention is that the insertion site of the device and means for deploying the expandable region from the first low-profile position to the second expanded position, as well as means for moving the clamping member toward the expandable region, are located remote from the anastomosis site. This remote location of these features allows for a less cluttered surgical field at the graft site itself, giving the surgeon a clearer field of view and more room to perform the procedure. Another of the many advantages of the invention is in the low-profile nature of the shaft assembly itself. By "low-profile" it is meant that the distal end of the shaft assembly, in its non-deployed, low-profile position, has a cross-sectional profile that is the same as, or only slightly larger, than the cross-sectional profile of remainder of the shaft assembly. This minimizes the size of the incision, puncture, or stick necessary to introduce the shaft assembly into the vessel and otherwise minimizes trauma to the vessel during insertion of the shaft assembly into the vessel. In many cases, the insertion site will be self-sealing upon removal of the assembly, or will otherwise at most require very minimal suturing. In addition, because the expanding region is deployable to its expanded position after its insertion into the vessel, the invention allows for the use of specific instrument configurations that would otherwise not be feasible to introduce directly through a vessel wall without unwarranted trauma to the vessel. For example, the specific configurations that are attainable by deploying the expanding region of the present invention after insertion into the vessel would otherwise require making large incisions to accommodate their introduction into the vessel.

In one embodiment of the invention, a shaft assembly is provided having a flexible tube extending over the shaft assembly with the distal end of the flexible tube secured to the distal end of the shaft assembly. The distal end of the flexible tube further includes an expanding region having bowing portions, with a sealing membrane attaching to the bowing portions. Movement of the flexible tube relative to the shaft assembly in the direction of the distal end of the assembly causes the bowing portions to bow outward, creating the expanded region of the assembly, with the sealing membrane spanning the expanded region.

In another embodiment of the invention, the shaft assembly includes a fixed shaft and a rotatable shaft that are axially aligned, each of which has corresponding bowing portions at the distal end of the respective shafts that extend away from the axis of the assembly. A sealing membrane is secured to and spans the bowing portions of the shafts. Rotation of the rotatable shaft causes the bowing portions of the shafts to become spaced apart from one another, creating an expanded region with the sealing membrane extending across the region.

Control of the deployment of the expandable region and movement of the clamping member toward the expandable region can either be operably linked or independent. In one embodiment of the invention, the clamping member includes an actuator that engages a slide that in turn engages the shaft assembly. Movement of the clamping member toward the expandable region moves the slide via the actuator, which then simultaneously moves the shaft assembly, resulting in the deployment of the expandable region. Alternatively, the invention also provides for deployment of the expandable region and movement of the clamping member independently. In one such embodiment, the shaft assembly includes the described axially aligned fixed and rotatable shafts which control deployment of the expandable region. The shaft assembly and clamping member are pivotally linked and also include handles, such that actuation of the handles moves the shaft assembly and clamping member independent of the expandable region deployment. In another embodiment, the clamping member is controlled by a turn screw mechanism and the deployment of the expandable region is controlled by an independent slide actuator.

In another embodiment of the invention, a device is provided having a housing with a clamping member pivotally mounted to the housing and a slide located within the housing and moveable from a first position to a second position. A shaft assembly is connected to the slide and extends therefrom. A flexible tube extends over the shaft assembly, the proximal end terminating near the housing and the distal end secured to the distal end of the shaft assembly. The distal end of the flexible tube includes an expanding region having first and second bowing portions, with a sealing membrane attaching to said bowing portions. The clamping member includes an actuator which engages the slide and a lever arm extending from the clamping member and terminating in a distal end defining a particular geometry. Upon movement of the clamping member, the actuator causes movement of the slide and shaft assembly, and the distal end of the flexible tube is displaced, forcing the bowing portions to bow outward, creating an expanded region of the tube with the sealing membrane stretched over the region. The distal end of the lever arm is shaped in a complementary pattern to the expanded region.

In use, the shaft assembly of a device according to the invention is introduced into the lumen of the aorta until the distal end of the tube is positioned beneath a target region at the graft site. A hole is created at the target region, either prior to or after positioning of the device. Actuation of the device clamps the vessel wall between the top clamp and expanded region of the flexible tube of the device, creating a seal against blood flow into the graft area. The surgeon can then proceed with performing the anastomosis in an essentially bloodless field.

In another embodiment of the invention, an occlusion device is provided having a shaft assembly and a clamping member pivotally mounted for movement toward and away from one another. The shaft assembly includes a fixed shaft and a rotatable shaft that are axially aligned, each of which has corresponding bowing portions at the distal end of the respective shafts that extend away from the axis of the assembly. A sealing membrane is secured to and spans the bowing portions of the shafts. Rotation of the rotatable shaft causes the bowing portions of the shafts to become spaced apart from one another, creating an expanded region with the sealing membrane extending across the region. The clamping member that is pivotally mounted for movement toward the shaft assembly includes a distal end having a configuration that corresponds to the expanded region of the shaft assembly when the bowing portions are in the described spaced apart configuration. In operation, the shaft assembly is introduced into the aorta, and then the bowing portions are deployed into the spaced apart configuration at the graft site. The clamping member is then moved toward the shaft assembly, clamping the vessel wall between the distal end of the clamping member and the distal end of the shaft assembly in the deployed, spaced apart configuration, creating a sealed off area for performing the graft.

In yet another embodiment of the invention, an occlusion device is provided having a housing with a slide located within the housing that is moveable from a first to a second position. A shaft assembly extends from the housing and includes a control rod extending through the length of the shaft assembly, an expandable region at the distal end of the shaft assembly, and a sealing membrane likewise at the distal end of the shaft assembly that spans the expandable region. The control rod is connected at its proximal end to the slide and at its distal end to the distal end of the shaft assembly. The expandable region is deployable from a first, low-profile position to a second expanded position. A clamping member is pivotally mounted to and extends from the housing. The distal end of the clamping member is shaped to correspond to the expandable region of the shaft assembly in its second expanded position. The device includes separate, independent actuators for deploying the expandable region of the shaft assembly into its expanded position and for pivotally moving the clamping member toward and away from the shaft assembly.

In another aspect of the invention, a lumen in fluid connection with an injection port and one or more delivery ports that open to the surface of the shaft assembly are provided, thus allowing for convenient means for delivering tissue adhesives, sealants or other agents to the anastomosis site, as well as allowing for general means of administering an agent into the bloodstream.

In yet another aspect of the invention, a filter is provided that is deployable downstream of the anastomosis site. The filter can collect and trap any debris or particulate matter that is loosened from the vessel wall during the anastomosis procedure.

In a further aspect of the invention, an occlusion device according to the invention is provided that is adapted for laproscopic use.

BRIEF DESCRIPTION OF THE DRAWINGS

FIG. 1 is a perspective view of an anastomosis occlusion device according to one embodiment of the invention, with the device in an open, non-occluding position;

FIG. 2 is a side view of the occlusion device of FIG. 1;

FIG. 2a is an end view of the occlusion device of FIG. 1;

FIG. 3 is a side view of the occlusion device of FIG. 1, with the device in a closed, occluding position;

FIG. 3a is an end view of the occlusion device of FIG. 3;

FIG. 4 is a perspective view of the occlusion device of FIG. 1, showing a shaft assembly portion of the device partially inserted into an aortic opening;

FIG. 6 is a perspective view of an anastomosis occlusion device according to a second embodiment of the invention;

FIG. 7 is an expanded view of the occlusion device of FIG. 6, with parts broken away, showing the distal end of the device in an expanded configuration for occlusion;

FIG. 8 is a perspective view of an occlusion device according to a third embodiment of the invention;

FIG. 9 is an expanded view of the device of FIG. 8, with parts broken away, showing an shaft assembly of the device in an expanded configuration;

FIG. 11 shows a cross-sectional side view of the device of FIG. 8;

FIG. 12 shows an expanded cross-sectional side view, with parts broken away, of the distal end of the shaft assembly of the device of FIG. 11;

FIG. 13 shows an introducer device for use with the device of FIG. 8; and

FIG. 14 shows a front end view of the introducer device of FIG. 13.

DETAILED DESCRIPTION OF THE INVENTION

Figure 3B:
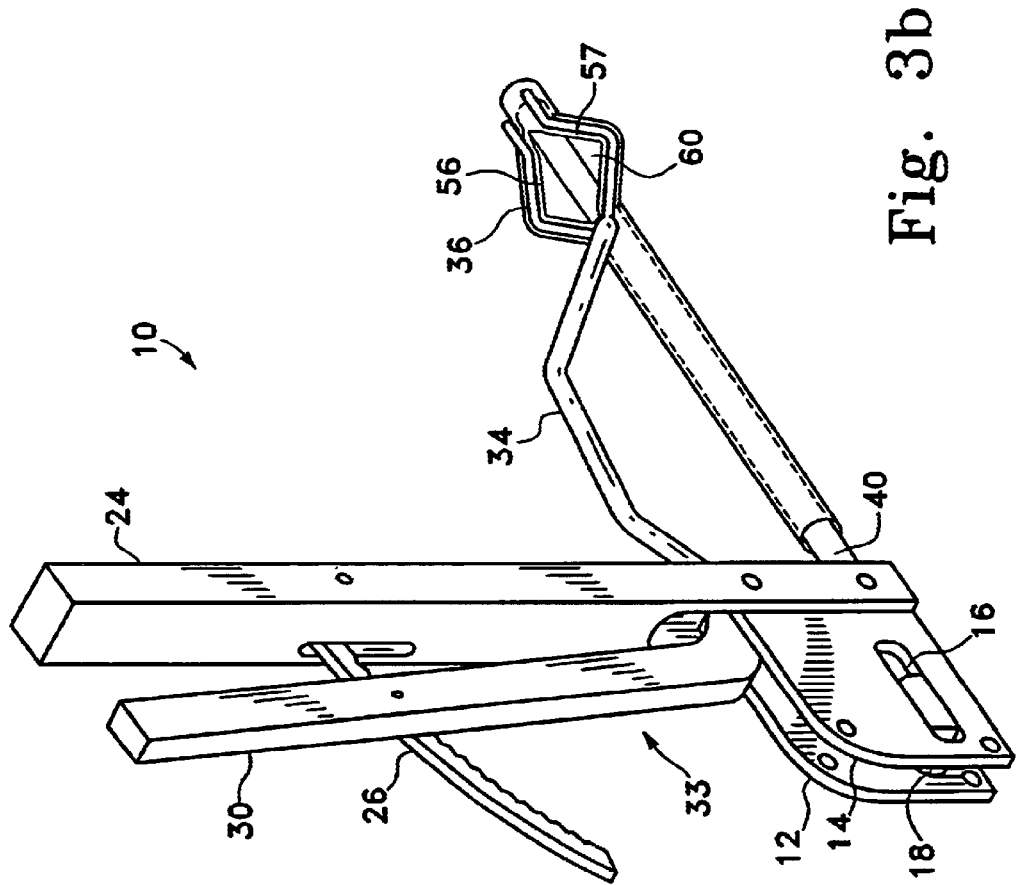
FIG. 3b is a perspective view of the occlusion device of FIG. 3.

FIGS. 1–5 depict one embodiment of an occlusion device according to the present invention. FIGS. 1, 2, and 2a show occlusion device 10 in the opened, non-occluding position. As seen, the device includes housing 20 formed of opposed plates 12 and 14. Slide 22 is slidably disposed within the housing and includes arms that extend into ports 16 and 18 of plates 12 and 14, allowing for linear translational movement of the slide relative to the housing. Shaft assembly 40 extends from slide 22, terminating at distal end 42 away from the housing. Clamping member 33 is positioned between plates 16 and 18 and is pivotally mounted to the housing by pivot 31, which may be a pin. The clamping member further includes lever 30, actuator 32, which engages slide 22 and remains disposed within the housing, and lever arm 34 which extends from the housing. Lever arm 34 terminates at its distal end in top clamping portion 36. Post 24 is secured to housing 20 in the same general plane as lever 30, shaft assembly 40 and lever arm 33. Post 24 includes ratchet 26 which matingly engages with lever 30.

As shown, shaft assembly 40 is surrounded by flexible tube 50. The shaft assembly 40 is preferably formed of rigid biocompatible material, such as stainless steel. The flexible tube is preferably made of a plastic, such as Hytrel™, having a durometer in the range of 60–90 Shore D and a length between 1" and 3". As shown in FIG. 2, three vertical through holes 51, 52, and 53 are drilled into the distal end, and a through slot 55 is cut through the tube, connecting the three holes. The distal tip of the shaft assembly 40, which remains located inside the flexible tube, is permanently secured to the distal tip of the flexible tube, but the remainder of the flexible tube is free to move relative to the shaft assembly 40. The proximal end of the flexible tube can be secured to the housing, or can otherwise abut up against the housing or terminate at a position near the housing, as shown in FIGS. 1 and 2. The proximal end of shaft assembly 40 is secured to slide 22. An elastomeric sealing membrane 60, essentially a sleeve and preferably formed of silicone, is secured around and along the length of the flexible tube. Alternatively, the sleeve can extend around the distal end of the tube, provided the sleeve covers that portion of the tube containing the holes 51, 52, and 53 and through slot 55. In the depicted embodiment, the wall thickness of the silicone is between 0.008" to 0.015", giving an overall diameter of shaft-flexible tube-sleeve cylindrical assembly in the range of 0.070" to 0.110", and the overall dimensions of the device are 3.5× 3.5×0.4" or less. One skilled in the art will appreciate that the dimensions can be varied to optimize performance based on the dimensions of the particular vessel to be occluded.

FIGS. 1, 2 and 2a depict device 10 in the open, non-occluding position. FIGS. 3, 3a, and 3b depict the device in the closed, occluded position. The device is actuated by moving lever 30 of clamping member 33 toward post 24. This motion has two effects. The first effect is that actuator 32 is thus displaced, forcing slide 22 to move laterally of the housing, away from the post. This in turn causes lateral displacement of shaft assembly 40 and forces the distal tip of flexible tube 50 to displace as well. The proximal end of flexible tube 50, however, is restrained by housing 20, so that the application of continued displacement force at the tip causes the bowing portions 56 and 57 to bow outwardly to accommodate tip displacement, as seen in FIGS. 3a and 3b. In the instant embodiment, the provision of holes 51, 52, and 53 weakens the relative rigidity of those corresponding regions of the tube, providing natural flex points along the two sides of the split portion of the tube, which allow for the bowing portions to bow outwardly into a predetermined pattern. In particular, the bowing portions of the instant embodiment expand into a diamond shape, although those skilled in the art will recognize that the invention contemplates arrangements of other flex points to create bowing portions that can displace into a variety of patterns. As also seen in FIGS. 3a and 3b, as the bowing portions expand outwardly, elastomeric sealing membrane 60 stretches to form a relatively planar sheet spanning the now created diamond pattern.

The other effect of moving lever 30 of clamping member 33 toward post 24 is that such movement causes lever arm 34 and top clamping portion 36 to be moved toward the now diamond shaped distal end of the flexible tube. As depicted, top clamping portion 36 is a wire form that matches and follows the contours of the outer edge of the expanded flexible tube. In the instant embodiment, top clamping portion 36 is diamond shaped, but in other embodiments, the clamping portion will be of a shape to match the pattern formed by the expanded distal end of the flexible tube, such as, but not limited to, round or oval shapes. Ratchet 26 engages lever 30 to lock the device in the closed position. The lever is spring loaded (not shown), allowing the device to return to its open position when the ratchet is disengaged.

The device of the present invention is designed for use in an off-pump procedure, with the heart beating and blood flowing through the aorta. As shown in FIG. 4, with device 10 in the open position, the shaft assembly 40 and flexible tube 50 assembly is inserted into the aorta (A) via an introduction hole (H). There are a variety of methods to accomplish such insertion. For example, the introduction hole can be created by a simple scalpel stick or needle puncture. Alternatively, a standard introducer can be employed, which would typically include a stylet, obturator and one-way hemostasis valve. Once the introducer is placed, the shaft assembly is passed through the introducer and into the aorta, and hemostasis is maintained by means of the introducer valve. In addition it may also be desirable to provide a guidewire passing through the introducer over which the shaft assembly can subsequently be passed and guided to the desired location. In such an event, the shaft assembly of the device can be hollow to accommodate the guidewire, or can otherwise be provided with one or more lumens to accommodate the guidewire.

Figure 5:
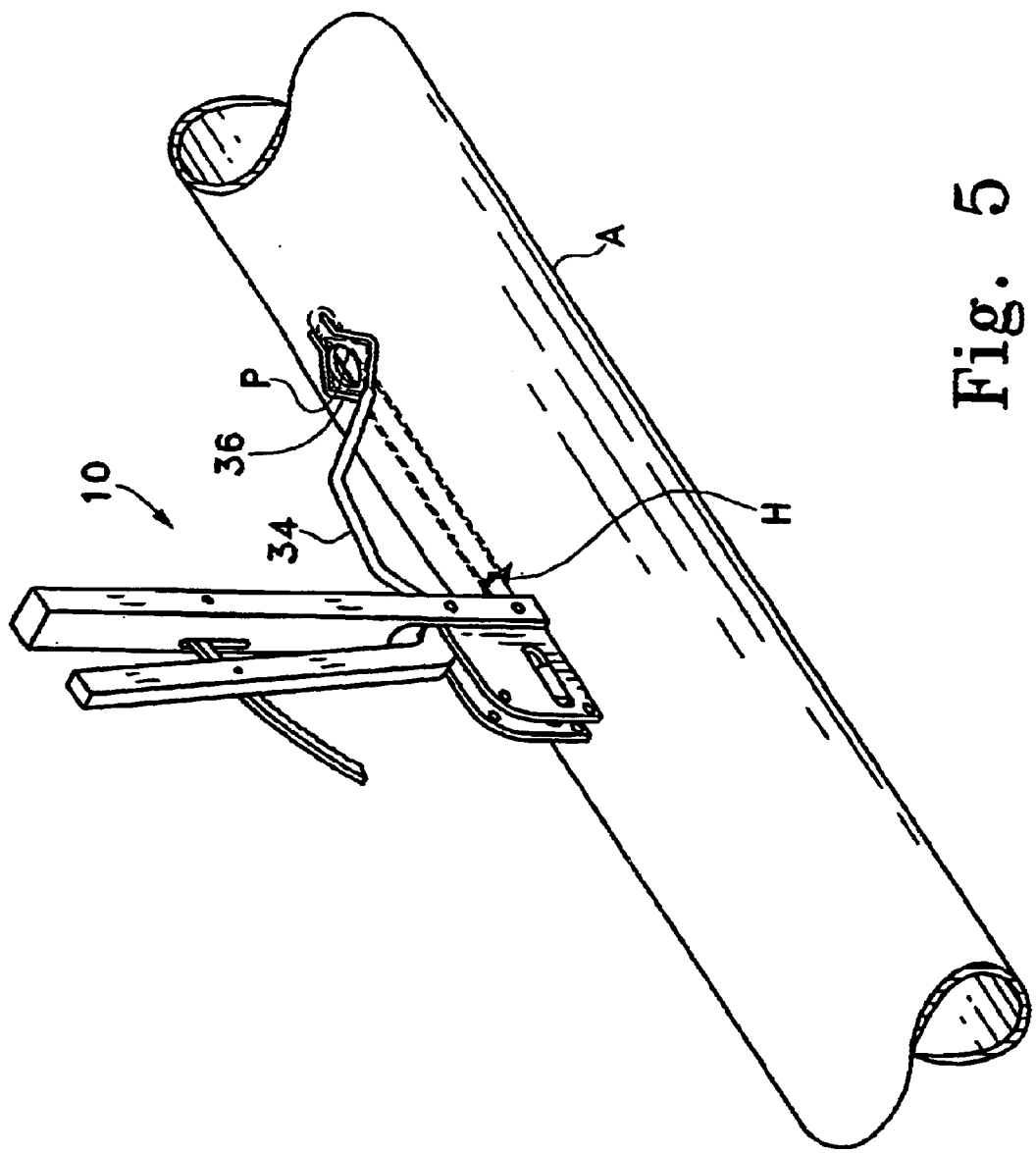
FIG. 5 is a perspective view of the occlusion device of FIG. 4, with the shaft assembly portion and clamp arm positioned at an anastomosis site of the aorta, and with the device in a closed, occluding position.

Using an arterial punch, hole (P) is then punched through the aorta at the intended site of grafting, and ahead of the distal tip of the device. As shown in FIG. 5, device 10 is further advanced such that the distal end of the flexible tube and top clamping portion of the lever arm 33 are over the hole. Alternatively, the device can first be deployed to the target site prior to punching the hole. Once positioned, the device is then actuated to its closed position. This results in the device "sandwiching" the vessel wall between the expanded flexible tube region and the top clamping portion. Stretched sealing membrane 60 seals blood from exiting the vessel through the punched hole. With the device secured in the closed position by means of the ratchet, a surgeon is now able to suture the graft around the circumference of the punched hole in a bloodless field. When the graft is sutured, the surgeon disengages the ratchet, returning the device to its open position, and removes the device through the introduction hole. Finally, the introduction hole is sutured closed.

As mentioned, methods of deploying the device of the invention can also incorporate, e.g., an introduction method using a hollow stainless steel shaft assembly. This facilitates guidewire introduction, a common technique used with catheters. The device can be introduced through the hollow shaft assembly, or if a guidewire has been deployed the device can be positioned by running the device over the guidewire. The invention also contemplates providing a kit that can include the device itself, as well as one or more of the following components: guidewire, introducer, introducer needle, dilator, aorta punch.

FIGS. 6 and 7 depict a second embodiment of the invention. In this embodiment, occlusion device 110 includes opposable clamping member 134 and shaft assembly 140 that are pivotally mounted for movement toward and away from one another. In particular, member 134 and shaft assembly 140 are connected at hinge 113, with handles 112 and 111 extending from clamping member 134 and shaft assembly 140, respectively. Actuation of the handles causes relative movement of the clamping member 134 and shaft assembly 140 toward or away from one another.

Shaft assembly 140 is further made up of two shafts 141 and 142 that are aligned with one another, as shown, along the axis of shaft assembly 140. The shafts 141 and 142 are of generally the same configuration and are coupled to one another by sleeves 145, 146, and 147. At the distal end of each shaft are bowing portions 156 and 157 which extend away from the axis defined by the shaft assembly 140 itself. Fixed shaft 141 is connected to handle 111. Rotatable shaft 142 is coupled to shaft 141 and remains free to rotate about the axis of the shaft assembly. Lever 130 extends from the proximal end of shaft 142. Sealing membrane 160 is secured to bowing portions 156 and 157.

By rotating shaft 142, bowing portions 156 and 157 of shafts 141 and 142 can be moved from an aligned position, where the portions are side by side, to an open, spaced-apart configuration where the bowing portions are opposite one another and define a plane and membrane 160 extends between the bowing portions. This open, spaced-apart configuration defines an expanded region at the distal end of the shaft assembly 140, with sealing membrane 160 spanning the region. Sealing membrane 160 can be formed of a variety of materials, provided they create an impermeable barrier. It is preferred, but not necessary, that the material have elastomeric properties, such as a silicone. Movement of lever 130, which is offset from shaft 142, provides a convenient way to rotate shaft 142 and position the bowing portions of the shafts 141 and 142 into the described spaced-apart configuration.

Clamping member 134, which is opposed to shaft assembly 140, includes a distal end having a clamping portion 136. Clamping portion 136 is configured to correspond to the shape of bowing portions 156 and 157 when in their expanded, spaced-apart configuration.

In operation, shaft assembly 140 is advanced into a vessel from a remote introduction hole with shafts 141 and 142 positioned such that the bowing portions 156 and 157 are aligned and side-by-side. In this low profile configuration, the shaft assembly 140 is easily introduced and advanced into the vessel. Once positioned at the target anastomosis site, lever 130 can be actuated by the surgeon, thereby rotating shaft 142 and creating the expanded region at the distal end of the assembly, with the sealing membrane spanning the expanded region. By actuating the handles of the device, member 134 can be moved toward shaft assembly 140, with clamping portion 136 of member 134 engaging the outer surface of the vessel and the expanded region of shaft assembly 140 engaging the inner surface of the vessel. A seal is then created at this clamped site, allowing the surgeon to proceed with performing a graft at the target site as described. When complete, the member and shaft assembly can be moved apart to release the seal, and shaft 142 rotated to return shaft assembly 140 into a low profile configuration for removal from the vessel.

FIGS. 8–11 depict a third embodiment of the invention, which is similar in some aspects to the first embodiment, but which further includes independent means for actuating the expanding region of the shaft assembly 240 and the clamping member 234. Occlusion device 210 includes housing 220, shaft assembly 240 and clamping member 234. Slide 222 is slidably disposed within the housing for linear translational movement from a first to a second position. Shaft assembly 240 includes control rod 241 disposed within flexible tube 250, with the proximal end of rod 241 being secured to slide 222. Clamping member 234 is pivotally mounted by pivot 231 to the housing, and terminates at its distal end in clamping portion 236. Slide actuator knob 228 and clamping member 234 actuator knob 227 are operably connected to slide 222 and member 234, respectively, as further described.

Flexible tube 250 can be formed of the same materials described above with respect to flexible tube 50 of FIGS. 1–5. Similarly, control rod 241 is preferably formed of a rigid biocompatible material, such as stainless steel. As in the embodiment of FIGS. 1–5, flexible tube 250 includes vertical through holes 251, 252, and 253 and through slot 255 cut through the tube from through hole 251 to through hole 253. Control rod 241 extends through the tube and is secured at its distal tip to the distal end of the flexible tube. Again, as in the embodiment of FIGS. 1–5, the remainder of the tube is free to move relative to the control rod, and the proximal end of the tube is secured to housing 220 or otherwise abuts against the housing or terminates at a position near the housing. Elastomeric sealing membrane 260, essentially a sleeve and preferably formed of silicone, extends around at least that part of the flexible tube that includes through slot 255. The thickness of the sleeve and the overall dimensions of the shaft assembly 240 are preferably as described above for the embodiment of FIGS. 1–5.

Figure 10:
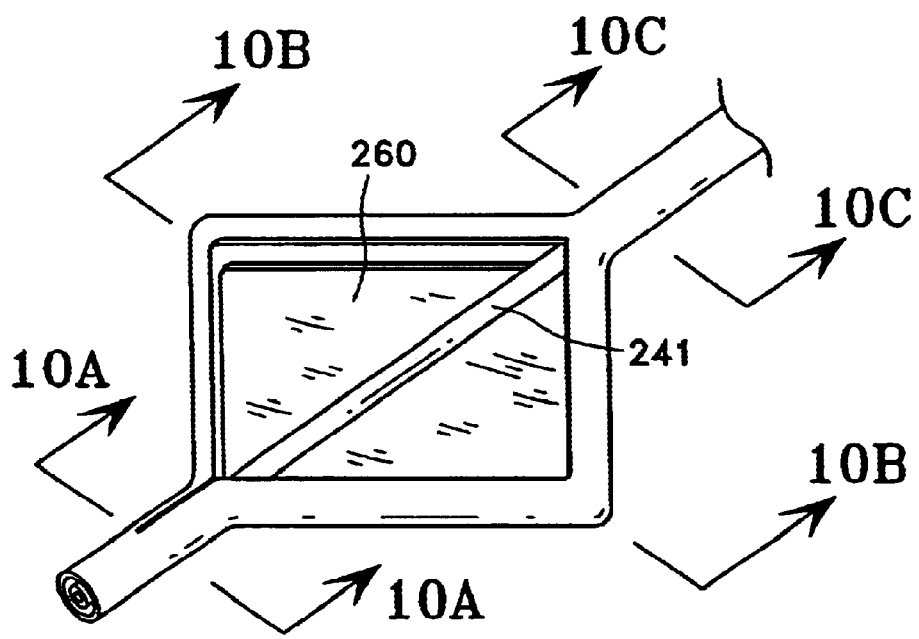
FIG. 10 shows another view of the shaft assembly of FIG. 9 in an expanded configuration.

FIGS. 9–10 show the distal end of occlusion device 210 in the expanded configuration. Such a configuration is achieved, much as with the embodiment of FIGS. 1–5, by lateral displacement of control rod 241. Displacement of control rod 241 forces the distal tip of flexible tube to likewise displace which in turn causes those portions of the flexible tube bisected by the through slot to bow outwardly in a predetermined pattern. The elastomeric sealing membrane 260 stretches to accommodate this movement, forming a planar sheet extending across the now expanded region of the distal end of the shaft assembly 240.

Figure 10A:
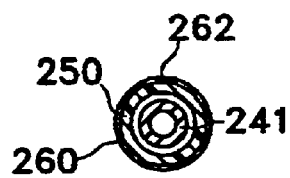
FIGS. 10A–10C show cross-sectional views of the shaft assembly of FIG. 10, taken along lines 10A–10A, 10B–10B and 10C–10C of FIG. 10, respectively.
Figure 10B:
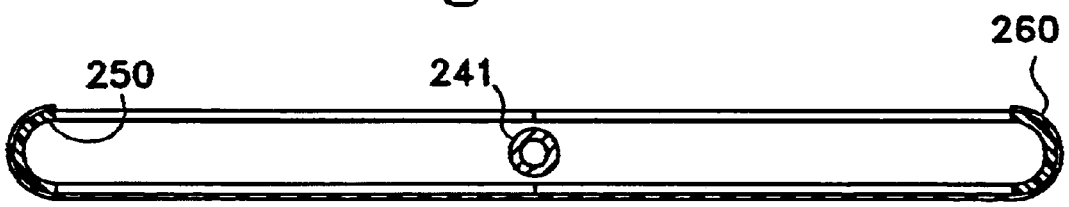
Figure 10C:
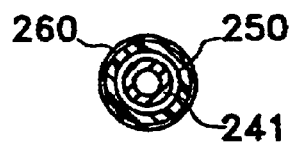

As depicted in FIGS. 10A–10C, at the distal end of the shaft assembly 240, the elastomeric sealing membrane 260 is not contiguous around the shaft assembly 240. Rather, a lengthwise gap 262 is provided in the sleeve, aligned with through slot 255 of the flexible tube 250. The remaining portion of the membrane 260 is adhered to the flexible tube 250. Upon deployment, as shown particularly in FIG. 10B, the elastomeric sealing membrane 260 stretches across the underside of the expanded region. In operation, when the shaft assembly 240 is deployed into a vessel and the top clamping portion of the clamping member 234 is compressed against the expanded region, a seal is created at the clamp site, just as with the embodiment of FIGS. 1–5. However, by this particular configuration of having the seal created by the sleeve being stretched only across the underside of the expanded region, a small space is created between the clamped vessel wall and the stretched sleeve. The provision of this space is advantageous to the surgeon, facilitating grafting procedures with less risk of puncturing the sleeve and breaking the seal.

As seen in FIG. 8 and more clearly in FIG. 11, occlusion device 210 includes separate actuating mechanisms for deploying the distal end of shaft assembly 240 into its expanded configuration and for moving top clamping portion 236 of clamping member 234 toward shaft assembly 240. As shown, slide actuator knob 228 is positioned external to the housing and has two spaced apart pins 281 and 282 that extend perpendicular to shaft assembly 240 and that are received by slide 222. In particular, slide 222 includes two cam portions 291 and 292 with receiving groove 293 in between. Pin 281 is received within groove 293, and pin 282 resides along the outer edge of cam portion 292, as shown when shaft assembly 240 is in the non-deployed position. A rotational force applied to slide actuator knob 228 causes pin 281 to engage the slide, resulting translation movement of the slide relative to the knob and the housing. Continued rotation moves the slide until such movement results in the shaft assembly being in the fully open or deployed condition, at which point pin 282 will have rotated all the way over and be in engagement with the outer edge of cam portion 291. In this position, as well as in the closed, non-deployed position, pins 281 and 282 are positioned horizontally, relative to the top and bottom of the housing, and the knob is stabilized against movement. A threshold rotational force is required to move the slide from either of these positions. In this manner, the knob acts to "lock" the shaft assembly in either the open, deployed, or the closed, non-deployed position.

Clamping member actuator knob 227 is located on the top portion of housing 220 and is axially connected to turn screw 271. Clamping member 234, is operably connected to turn screw 271 by link 272. Rotation of actuator knob 227 turns the turn screw which raises or lowers arm 234 about pivot 231, and thus moves top clamping portion 236 toward or away from shaft assembly 240. Gear 273 is likewise axially connected to knob 227 and gear teeth along the gear circumference engage spring member 274. The gear and spring member assembly allows the turn screw to be incrementally rotated, in either direction, in a controlled manner. In this way, the force applied by the top clamping portion to a clamped vessel can be finely calibrated.

Occlusion device 210 can be inserted into a vessel and deployed similar to methods described above for the embodiment of FIGS. 1–5. As described, however, the expansion of the distal end region of shaft assembly 240, and the movement of clamping member 234 and top clamping portion 236 to clamp a vessel wall between expanded region of the shaft assembly and the top clamping portion, are performed independently, through the rotation of slide actuator knob 228 or clamping member actuator knob 227. As seen in FIG. 8, occlusion device 210 can further be provided with bleed back tube 233 and luer lock 232. Observance of a backflow of blood from the bleed back tube confirms that the deployed shaft assembly is positioned within the lumen of the target blood vessel. The luer lock can then be engaged to stop further flow. Alternatively, a porous vent can be inserted which will allow air but not blood to escape.

Alternatively, as shown in FIGS. 11–12, occlusion device 210 can be provided with stylet 290 that can be advanced through shaft assembly 240 and extended from the distal end of the shaft assembly. The stylet can be used to create the entry hole in the vessel for entry of the shaft assembly, such that the creation of the entry hole and the insertion of the shaft assembly into the vessel can be accomplished in a single, convenient step. More particularly, control rod 241 is provided with a lumen extending throughout the length of the rod. Stylet 290 is advanced through luer lock 232, at the rear of the housing, and passed through the lumen of control rod 241 until the tip of the stylet extends from the distal end of shaft assembly 240, as shown more clearly in FIG. 12. Once the blood vessel has been pierced and the shaft assembly at least partially advanced into the blood vessel lumen, the tip of the stylet can be withdrawn into the control rod lumen to avoid the possibility of injury or trauma to the vessel.

FIGS. 13–14 depict a removable introducing device adapted for use with occlusion device 210. As shown, introducing device 300 includes half-tube 302 which is essentially hemicylindrical. The distal end 303 of the half-tube is beveled, providing a sharp point capable of piercing tissue. The proximal end of half-tube 302 is attached to housing 304. Housing 304 is configured to matingly engage with the bottom portion of housing 220 of device 210, whereby housing 304 can be held under tension against bottom portion of housing 220. As shown, housing 304 includes spring clip 312 that extends from base 306 of housing 304. Sidewalls 308 and 309 extend upwardly from base 306 and include retaining lips 314 and 315 that extend inwardly from the top of the sidewalls. As shown in FIG. 8, ridges 229 and 231 extend outwardly from either side of the bottom portion of housing 220. Occlusion device 210 can be secured to introducer device 300 by pressing down on spring clip 312 while sliding ridges 229, 231 of the occlusion device under retention lips 314, 315. The force supplied by spring clip 312 keeps ridges 229 and 231 of the occlusion device engaged with and retained against retention lips 314 and 315. Half-tube 296 of introducing device 300 corresponds to shaft assembly 250 of occlusion device 210 with a slightly wider diameter, such that shaft assembly 250 is received within half-tube 296. The distal end 297 of the half-tube extends beyond the distal end of the shaft assembly 250. The introducing device allows the vessel wall to be pierced and the occlusion device inserted with a single motion. The introducing device can then be removed, leaving the shaft of the occlusion device deployed within the vessel lumen.

A device according to the invention can further include a filter deployable from the distal end of the device that can be used to trap, collect and remove any debris that is loosened from the vessel wall during the deployment and use of the device. The filter can conveniently be formed of a mesh, screen or filter material that will trap particulate matter while allowing blood to pass through the filter. Suitable materials for forming the filter include, e.g., a thermoplastic or stainless steel mesh, or a porous elastomeric membrane. The filter can be deployed through, e.g., a hollow shaft assembly of the device, or a lumen otherwise provided through the shaft assembly. Alternatively, the filter can be deployed separately from deployment of the occlusion device of the invention and used in conjunction therewith.

Various types of filters are contemplated by the invention. One such embodiment includes a tubular sock shaped mesh net extending from a loop structure. The loop structure can be offset from a guidewire. Typical filters having such a general configuration are FILTERWIRE™ embolic filters (Embolic Protection, Inc., Campbell, Calif.). In the present invention, the loop can be formed of a deformable shape memory alloy, allowing it to be passed through or retained in a lumen of the shaft assembly of the occlusion device. In operation the filter is deployed downstream of the anastomosis site. It is preferred that the loop diameter conform as much as possible to the inner diameter of the vessel, in order to maximize the chance to trap any loosened debris. Once the procedure is complete, the filter can be withdrawn back into the lumen of the occlusion device, or, if the volume of collected debris makes such withdrawal unfeasible, the occlusion device can first be removed from the vessel, followed by the filter. In another embodiment of a filter according the present invention, the filter has a configuration similar to an umbrella and is again deployable through the lumen of the occlusion device. In a filter according to this embodiment, an offset central elongated support is extendable from the lumen. Mesh is secured to ribs radially extending from the distal end of the elongated support and are further attached to a longitudinally moveable portion of the support such that the filter can be "opened" once deployed in the lumen vessel to span the inner diameter of the vessel. Again, after completion of the procedure, the filter can be "closed" thus trapping the collected debris and, depending on the volume of debris collected, either retracted back into the lumen of the occlusion device or removed from the vessel separately. In yet another embodiment of a filter according to the invention, mesh of a generally hemispherical configuration can be attached to a plurality of tethers, much like a parachute, and deployed from the lumen of the occlusion device.

As mentioned, the shaft assembly can be hollow or otherwise provided with one or more lumens to facilitate the use of a guidewire or debris filter. Such passageways or lumens can also be employed for delivery of fluids or other agents to the anastomotic site, or elsewhere along the shaft assembly. Delivery ports that open to the shaft assembly surface are provided that are in fluid communication with the passageways or lumens. An injection port is likewise provided at the proximal end of the shaft assembly in fluid communication with a passageway or lumen, as is typically found in, e.g., a fluid delivery catheter or similar device. Of particular interest is the delivery of tissue adhesives, i.e., glues, and tissue sealants to the anastomosis site. Suitable tissue adhesives include protein-based surgical adhesives, such as BIOGLUE™ brand surgical adhesive (which contains albumin and glutaraldehyde) (CryoLife, Kennesaw, Ga.). Suitable tissue sealants include thrombin based products, such as FLOSEAL™ sealant (collagen and thrombin) (Fusion Medical Technologies, Fremont, Calif.), COSTASIS™ sealant (collagen and thrombin)(Cohesion Technologies, Palo Alto, Calif.), and TISSEEL™ sealant (fibrin and thrombin) (Baxter). The administration of these tissue adhesives and sealants at the anastomosis site aids in control leakage around the grafted vessel. In addition, a wide variety of other useful agents or biomaterials can be similarly delivered, including hemostatic agents, coagulants, or therapeutic or diagnostic agents, including both those used in association or conjunction with the anastomosis procedure itself, and those used for related or even unrelated conditions and procedures.

In addition, the invention also contemplates an occlusion device configured for introduction to the graft site and manipulation via laproscopic techniques, thereby allowing for closed-chest coronary artery bypass grafting. Such a device will have a further reduced profile capable of passing through a standard laproscopic port, and will preferably be configured such that the actuating mechanisms for activating the expanding region and clamping member are located remote from the shaft assembly and clamp member, thereby facilitating laproscopic use of the device. As an example, device 210 of FIG. 8 can be easily adapted for laproscopic deployment. For example, turn screw 272 and associated structures can be reoriented to provide a sleeker overall profile to the device, thereby accommodating insertion through a laproscopic port. Actuator knobs 227 and 228 can be adapted for receiving cables that extend remotely from the device. The slide and clamping member actuators can then be remotely activated while the device is laproscopically deployed via external manipulation of the cables. Alternative ways to remotely operate the device while laproscopically deployed include, e.g., the provision of slide and clamping members that are activated by pistons that are operable through the provision of, e.g., compressed air or gas. Again, in such a configuration, conduits in fluid communication with the pistons can extend remotely from the device and air or gas can be delivered externally via the conduits to drive the pistons and activate the device.

While particular embodiments of the invention have been described above, the invention is not intended to be limited to such, but rather one skilled in the art will recognize that many modifications may be made that still remain within the scope of the invention, as defined by the appended claims.

We claim:

1. An occlusion device for an anastomosis procedure comprising:
    a low profile shaft assembly configured for insertion into a vessel, said shaft assembly having an expandable region at the distal end of the shaft assembly and a sealing membrane spanning said expandable region, said expandable region being deployable from a first low-profile position to a second expanded position;

means for deploying said expandable region from said first low-profile position to said second expanded position; and a clamping member positioned generally opposite to and moveable towards said expanding region, said clamping member having a distal end shape corresponding to said expanding region in its second expanded position.

2. The occlusion device of claim 1 wherein said expandable region includes the expandable region bowing portions that bow outward.

3. The occlusion device of claim 2 wherein said bowing portions further comprise a flexible tube having a through slot.

4. The occlusion device of claim 1 wherein said means for deploying said expandable region and said clamping member are operably linked, such that movement of the clamping member simultaneously activates said expandable region deployment means.

5. The occlusion device of claim 1 wherein said means for deploying said expandable region and said clamping member operate independently of one another.

6. An occlusion device for an anastomosis procedure comprising:

a housing having a slide located therein, said slide mounted to said housing and moveable from a first position to a second position;

a rigid shaft assembly connected to the slide and having a portion thereof extending from the housing;

a clamping member pivotally mounted to the housing, said member having a slide actuator engaged with said slide, and a lever arm extending from the housing and terminating in a distal end defining a first planar geometry;

a flexible tube extending over said extending portion of said shaft assembly, said tube having a proximal end terminating near the housing, a distal end, and an expanding region proximal to the distal end, said expanding region having first and second bowing portions and an elastomeric sealing membrane over said bowing portions;

wherein pivotal movement of the clamping member moves said slide from said first position to said second position, thereby moving said rigid shaft assembly from a first to second position and causing said bowing portions to expand outward from said shaft assembly.

7. The occlusion device of claim 6 wherein said expanding region is defined by a slot extending through the flexible tube to form said first and second bowing portions.

8. The occlusion device of claim 6 wherein said pivotal movement of the clamping member further results in movement of said lever arm toward said expanding region.

9. The occlusion device of claim 8 wherein said shaft assembly further includes a lumen in fluid connection with an injection port at the proximal end of the device and one or more delivery ports opening to the surface of the shaft assembly.

10. The occlusion device of claim 6 further comprising a post extending from said housing, and wherein said clamping member further includes a lever, said post having a ratchet that matingly engages with said lever to lock the device in a closed position.

11. The occlusion device of claim 6 wherein said shaft assembly further includes a lumen in fluid connection with an injection port at the proximal end of the device and one or more delivery ports opening to the surface of the shaft assembly.

12. The occlusion device of claim 6 wherein said shaft assembly further includes a lumen extending through the shaft assembly and opening to the distal end of the shaft assembly, and a filter for capturing debris released during the procedure, wherein the filter is adapted for containment within the shaft assembly lumen and deployment from the shaft assembly distal end.

13. An occlusion device for an anastomosis procedure comprising:

a shaft assembly and a clamping member pivotally mounted for movement toward and away from one another, said shaft assembly defining a longitudinal axis and including a fixed shaft and a rotatable shaft aligned along said axis, each having corresponding bowing portions at a distal end of said shaft assembly that extend away from said axis, and a sealing membrane secured to said bowing portions of said shafts;

whereby when said rotatable shaft is rotated, said bowing portions become spaced apart into a spaced apart configuration, creating an expanded region wherein said sealing membrane spans said region; and said clamping member having a distal end having a clamping portion, said clamping portion configured to said bowing portions when in said spaced apart configuration.

14. An occlusion device for an anastomosis procedure comprising a housing having a slide located therein, said slide moveable from a first to a second position;

a shaft assembly extending from said housing, said shaft assembly having a rod extending through the shaft, an expandable region at the distal end of the shaft assembly, and a sealing membrane spanning said expandable region of the shaft assembly, the rod being connected at one end to said slide and at its other end to the distal end of the shaft, and the expandable region being deployable from a first, low-profile position to a second expanded position;

a member comprising a clamping member pivotally mounted to said housing and extending therefrom, said clamping member having a distal end shape corresponding to said expandable region in its second expanded position.

15. The device of claim 14 further comprising a slide actuator capable of moving said slide from said first to said second position.

16. The device of claim 15 wherein said slide actuator further comprises two cam portions having inner and outer edges, said inner edges defining a receiving groove between said cam portions, and wherein said slide actuator further comprises a knob having first and second pins extending therefrom, said first pin being received within said receiving groove and said second pin being received alongside one of said outer edges, whereby upon rotational movement of said knob, said first pin engages said slide causing translational movement of said slide from said first position to said second position, and said second pin moves relative to said slide from the outer edge of said first cam portion to the outer edge of said second cam portion.

17. The device of claim 16 wherein said slide is capable of being locked in said first or second position.

18. The device of claim 15 wherein said slide actuator is activatable from a location remote from the shaft assembly.

19. The device of claim 14 further comprising a clamping member actuator capable of pivotally moving said member.

20. The device of claim 19 wherein said clamping member actuator comprises a turn screw operably linked to said member such that rotation of said screw pivotally moves said member.

21. The device of claim 19 wherein said clamping member actuator is activatable from a location remote from the clamping member.

22. The device of claim 14 further comprising a bleed back tube placed in fluid connection with said shaft assembly.

23. The occlusion device of claim 14 wherein said shaft assembly further includes a lumen in fluid connection with an injection port at the proximal end of the device and one or more delivery ports opening to the surface of the shaft assembly.

24. The occlusion device of claim 14 wherein said shaft assembly further includes a lumen extending through the shaft assembly and opening to the distal end of the shaft assembly, and a filter for capturing debris released during the procedure, wherein the filter is adapted for containment within the shaft assembly lumen and deployment from the shaft assembly distal end.

25. A method of partially occluding a vessel comprising the the steps of
   providing an occlusion device according to any one of claims 1, 6, 13 or 14;
   forming a hole in the vessel;
   advancing the shaft assembly of the device through the hole and into the vessel;
   deploying the expandable region of the shaft assembly from the first low-profile position to the second expanded position; and
   moving the clamping member toward the expanded region until the distal end of the clamping member engages the outer surface of the vessel and the expanded region engages the inner surface of the vessel, thereby creating a sealed-off, partially occluded area of the vessel.

26. A method of performing an anastomosis procedure comprising the steps of:
   providing an occlusion device according to any one of claims 1, 6, 12 or 14;
   identifying a target site on a first vessel for a grafting a second bypass vessel thereto;
   forming a first hole in the first vessel remote from the target site;
   advancing the shaft assembly of the device through the hole and into the first vessel until the expandable region is positioned at the target site;
   forming a second hole in the first vessel at the target site;
   deploying the expandable region of the shaft assembly from the first low-profile position to the second expanded position;
   moving the clamping member toward the expanded region until the distal end of the clamping member engages the outer surface of the vessel and the expanded region engages the inner surface of the vessel, thereby creating a sealed-off area at the target site; and
   grafting the bypass vessel to the first vessel at the target site.

27. An introducer device for introducing the shaft assembly of the occlusion device of claims 1, 6, 13, or 14 into the lumen of a vessel, the introducer device comprising a base portion adapted for mating engagement with the housing of the occlusion device and a hemicylindrical guide for receiving the shaft assembly of the occlusion device, the hemicylindrical guide having a sharpened distal end for piercing tissue.

28. A system for use in performing an anastomosis procedure comprising the occlusion device of claims 1, 6, 13, or 14 and a filter adapted for deployment within a vessel lumen to capture debris released during the procedure.

29. An occlusion device for an anastomosis procedure comprising:
   a low profile shaft assembly configured for insertion into a vessel, said shaft assembly having an expandable region at the distal end of the shaft assembly and a sealing membrane spanning said expandable region, said expandable region being deployable from a first low-profile position to a second expanded position, and wherein said shaft assembly further includes a lumen in fluid connection with an injection port at the proximal end of the device and one or more delivery ports opening to the surface of the shaft assembly;
   means for deploying said expandable region from said first low-profile position to said second expanded position; and
   a clamping member positioned generally opposite to and moveable towards said expanding region, said clamping member having a distal end shape corresponding to said expanding region in its second expanded position.

30. An occlusion device for an anastomosis procedure comprising:
   a low profile shaft assembly configured for insertion into a vessel, said shaft assembly having an expandable region at the distal end of the shaft assembly and a sealing membrane spanning said expandable region, said expandable region being deployable from a first low-profile position to a second expanded position, and wherein said shaft assembly further includes a lumen extending through the shaft assembly and opening to the distal end of the shaft assembly, and a filter for capturing debris released during the procedure, wherein the filter is adapted for containment within the shaft assembly lumen and deployment from the shaft assembly distal end;
   means for deploying said expandable region from said first low-profile position to said second expanded position; and
   a clamping member positioned generally opposite to and moveable towards said expanding region, said clamping member having a distal end shape corresponding to said expanding region in its second expanded position.

* * * * *